(12) United States Patent
Piironen et al.

(10) Patent No.: US 6,327,374 B1
(45) Date of Patent: Dec. 4, 2001

(54) ARRANGEMENT AND METHOD FOR INSPECTION OF SURFACE QUALITY

(75) Inventors: Timo H. Piironen, Oulu (FI); Detlef Paul, München (DE); Pertti Kontio, Oulu (FI)

(73) Assignees: Thermo Radiometrie Oy; Fraunhofer-Gesellschaft zur Forderung der Angewandten Forschung E.V., both of Munich (DE)

( * ) Notice: Subject to any disclaimer, the term of this patent is extended or adjusted under 35 U.S.C. 154(b) by 0 days.

(21) Appl. No.: 09/252,011

(22) Filed: Feb. 18, 1999

(51) Int. Cl.$^7$ ........................................... G06K 9/00
(52) U.S. Cl. .............................................. 382/108
(58) Field of Search ...................... 382/100, 108, 382/165, 141, 154, 162, 163, 312, 317, 318, 325; 356/484, 485, 371, 429, 430, 431, 237.1, 238.1; 348/86, 92, 91, 125, 128, 131, 132, 133, 134, 195, 207, 260, 262, 335, 342, 362, 363, 366, 367, 370; 354/126, 127.1, 129, 132; 396/20, 155, 166, 167, 172, 175, 180, 182

(56) References Cited

U.S. PATENT DOCUMENTS

| H1616 | * 12/1996 | Wolfe ........................................ 348/88 |
| 3,892,492 | 7/1975 | Eichenberger ........................ 356/434 |

(List continued on next page.)

FOREIGN PATENT DOCUMENTS

| 195 534 | 10/1996 | (DE) | ............................. G01N/21/88 |
| 197 20 308 | 11/1998 | (DE) | ............................. G01N/21/89 |
| 59-52735 | 3/1984 | (JP) | ............................. G01N/21/88 |
| 4-279848 | 10/1992 | (JP) | ............................. G01N/21/89 |
| WO 92/00517 | 1/1992 | (WO) | ............................. G01N/21/89 |
| WO 94/18643 | 8/1992 | (WO) | ............................. G01N/9/00 |

OTHER PUBLICATIONS

"Familiar Aspects of the Interaction of Light and Matter" Book of Optics by Hecht, 1998, sec. 4.9, pp. 131–135.*

06058731 "Patent Abstracts of Japan", March 1994, Yoshinori Pattern Inspecting Apparatus.

"Determining Surface curvature with Photometric Stereo" by Woodham, 1989 IEEE Intl. Conf. On Robotics and Automation.

*Primary Examiner*—Andrew W. Johns
*Assistant Examiner*—Shervin Nakhjavan
(74) *Attorney, Agent, or Firm*—Sughrue, Mion, Zinn, Macpeak & Seas, PLLC (57) ABSTRACT

The invention relates to a method for automatic inspection of the surface 20 of a moving object, in which a region on the object's surface is illuminated from at least two different illumination directions 13–15. The object's illuminated surface region is imaged with a camera to provide image information for analysis. The light sources in the different illumination directions 13–15 are pulsed to illuminate the object's surface region at different times, the pulsing frequency being >1 kHz The object's illuminated surface region is imaged as lines with a line scan camera 21 in sync with the above pulsing. The invention also relates to an arrangement for inspecting the surface 20 of a moving object, the arrangement comprising at least two light sources 10–12 in at least two different illumination directions 13–15 for illuminating the surface region of the object under inspection; a camera for imaging the object's surface region; and an image analyzer for analyzing the image information acquired from the object's surface 20 by imaging. The light sources 10–12 illuminate the object's surface 20 from the different illumination directions 13–15 at different times, and the camera is a line scan camera 21. The arrangement further comprises a timing controller 18 for synchronous pulsing of the light sources 10–12 and the at least one line scan camera 21, the pulsing frequency of the light sources 10–12 being >1 kHz.

65 Claims, 10 Drawing Sheets

U.S. PATENT DOCUMENTS

| | | | |
|---|---|---|---|
| 5,039,868 | 8/1991 | Kobayashi et al. | 250/559.08 |
| 5,298,963 | 3/1994 | Moriya et al. | 356/31 |
| 5,365,084 | 11/1994 | Cochran et al. | 250/559.03 |
| 5,870,180 * | 2/1999 | Wangler | 356/401 |
| 5,960,104 * | 9/1999 | Conners et al. | 382/141 |
| 6,044,170 * | 3/2000 | Migdal et al. | 382/154 |
| 6,122,065 * | 9/2000 | Gauthier | 356/394 |

* cited by examiner

ARRANGEMENT AND METHOD FOR INSPECTION OF SURFACE QUALITY

FIELD OF INVENTION

The invention relates to inspection of strip-like or sheet-like surfaces, such as surfaces of rolled metal products, by an optoelectronic measuring arrangement.

BACKGROUND OF INVENTION

DE 19 511 534 A1 teaches a prior art method and arrangement in which the 3D characteristics of a moving surface are inspected by illuminating the surface from at least two different illumination directions with light sources, the light sources of each illumination direction illuminating the surface with a light of a different color than the other illumination directions. The object's surface is illuminated simultaneously from the different illumination directions, and the so illuminated surface is imaged with a camera to provide image information for analysis. The analysis of the 3D characteristics of the object's surface is based on color classification, with which the color values detected on the surface are compared.

The prior art method and arrangement allow the inspection of the 3D characteristics of the object's surface but not of the glossiness and reflectivity of the surface, since symmetrical dark field illumination from two illumination directions is used in the method. The fact that the 3D analysis is based on color classification impairs the method: for example, the method is not able to adjust to a change in the surface material of the object's surface, in which the surface material changes either completely or changes to a different variety of the same surface material or both, and neither is it able to adjust to changes in the illumination. This causes false alarms, which poses a major problem particularly in production processes.

On account of the above, the prior art method thus has a very limited ability to differentiate between different anomalies on the object's surface.

BRIEF DESCRIPTION OF INVENTION

The object of the invention is to provide a method and an arrangement implementing the method, simultaneously solving the above problems. The object is achieved with a method of the invention for automatic inspection of the surface of a moving object, the method comprising the steps of illuminating a region on the object's surface with light sources from different illumination directions, and imaging the object's illuminated surface region with a camera to provide image information for analysis. The light sources in the different illumination directions are pulsed to illuminate the object's surface region at different times, the pulsing frequency being >1 kHz. Further, the object's illuminated surface region is imaged as lines with a line scan camera in sync with the above pulsing. If colors are not considered relevant, the line scan camera used can be a monochrome camera. If colors are also to be measured, the line scan camera used is a color camera.

The invention also relates to an arrangement for inspecting the surface of a moving object, the arrangement comprising at least two light sources in at least two different illumination directions, i.e. at least one light source in each illumination direction used, for illuminating a surface region of the object under inspection; a camera for imaging the object's surface region; and an image analyzer for analyzing the image information acquired from the object's surface by imaging. As regards the light sources, the arrangement comprises light sources that illuminate the object's surface at different times from different illumination directions. To take images from the surface, the arrangement comprises at least one line scan camera. The arrangement also comprises a timing controller for synchronous pulsing of the light sources and the at least one line scan camera, the pulsing frequency being >1 kHz.

The preferred embodiments of the invention are claimed in the dependent claims.

The invention is based on the idea that the light sources in the different illumination directions are pulsed to illuminate the object's surface region at different times, the pulsing frequency being >1 kHz, and that the object's illuminated surface region is imaged as lines with a line scan camera in sync with the pulsing.

Various advantages are achieved with the method and arrangement of the invention. The invention allows image analysis, in which the objects surface region, imaged while illuminated at different times with light beams from different illumination directions, is inspected. This enhances the analysis of the 3D characteristics of the surface considerably, since the object's surface region imaged while illuminated at different times with light beams from different illumination directions reveals more of its 3D characteristics than when it is illuminated simultaneously from different illumination directions. In addition to enhancing the analysis of the 3D characteristics, the non-simultaneous illumination also enhances inspection of the glossiness and reflectivity of the surface. The invention also allows the inspection of the surface of a fast moving object since the inversion comprises fast synchronous pulsing of the light sources and the line scan camera.

The preferred embodiments of the invention and other implementations described in detail emphasize the advantages of the basic invention and also bring about other advantages. The surface inspection shows the colors correctly, which renders the 3D analysis, glossiness analysis and reflectivity analysis of the surface more accurate. When the accuracy is improved, for example, false alarms are avoided, which greatly speeds up the production process. Further, a preferred embodiment of the invention introduces an improved way of inspecting a moving surface from a distance, for example a hot moving surface. The surface inspection from a distance here means that the surface is inspected from a distance of at least one meter, perhaps even of three meters.

BRIEF DESCRIPTION OF FIGURES

In the following the invention will be described in greater detail by means of preferred embodiments and with reference to the attached drawings, in which.

DETAILED DESCRIPTION OF INVENTION

Figure 1:
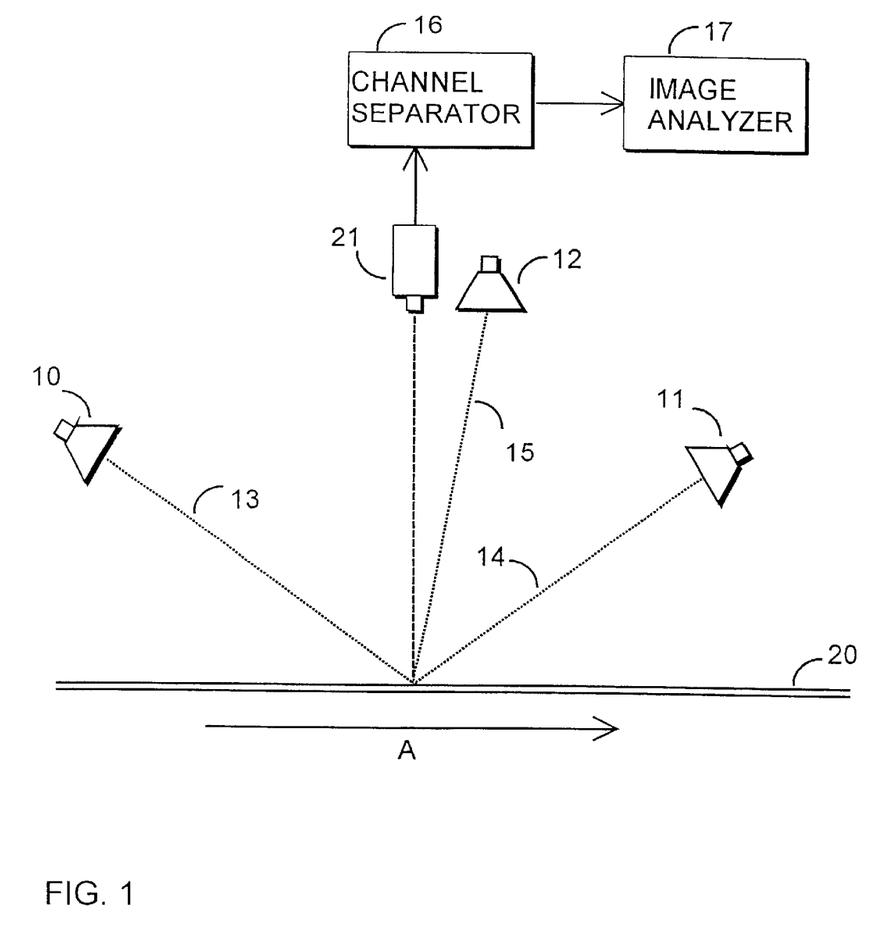
FIG. 1 shows an arrangement with one line scan camera.

FIG. 1 shows an arrangement for inspecting the quality of a surface 20 of a moving object. The movement of the object is indicated by arrow A. In a preferred embodiment the surface inspected is a strip-like surface or a sheet-like surface, for example a surface of a rolled metal product. The arrangement comprises light sources 10–12 of at least two—in the figure, three—illumination directions 13–15 for illuminating a region on the object's surface, and a line scan camera 21 for imaging the illuminated surface region. The arrangement further comprises a channel separator 16 for performing channel separation on the output signal of the line scan camera 21, and a image analyzer 17 for analyzing the image information obtained from the channel separator.

In FIG. 1 the surface 20 of the moving object is illuminated with light sources 10–12 of at least two different illumination directions 13–15. The illuminated region on the object's surface is imaged with the line scan camera 21, and the output signal acquired from the line scan camera 21 is subjected to channel separation in the channel separator 16. On the basis of the image information contained in the channel-separated channels CH1, CH2, etc. an image analysis is performed in the image analyzer 17 to inspect the object's surface 20.

Figure 2:
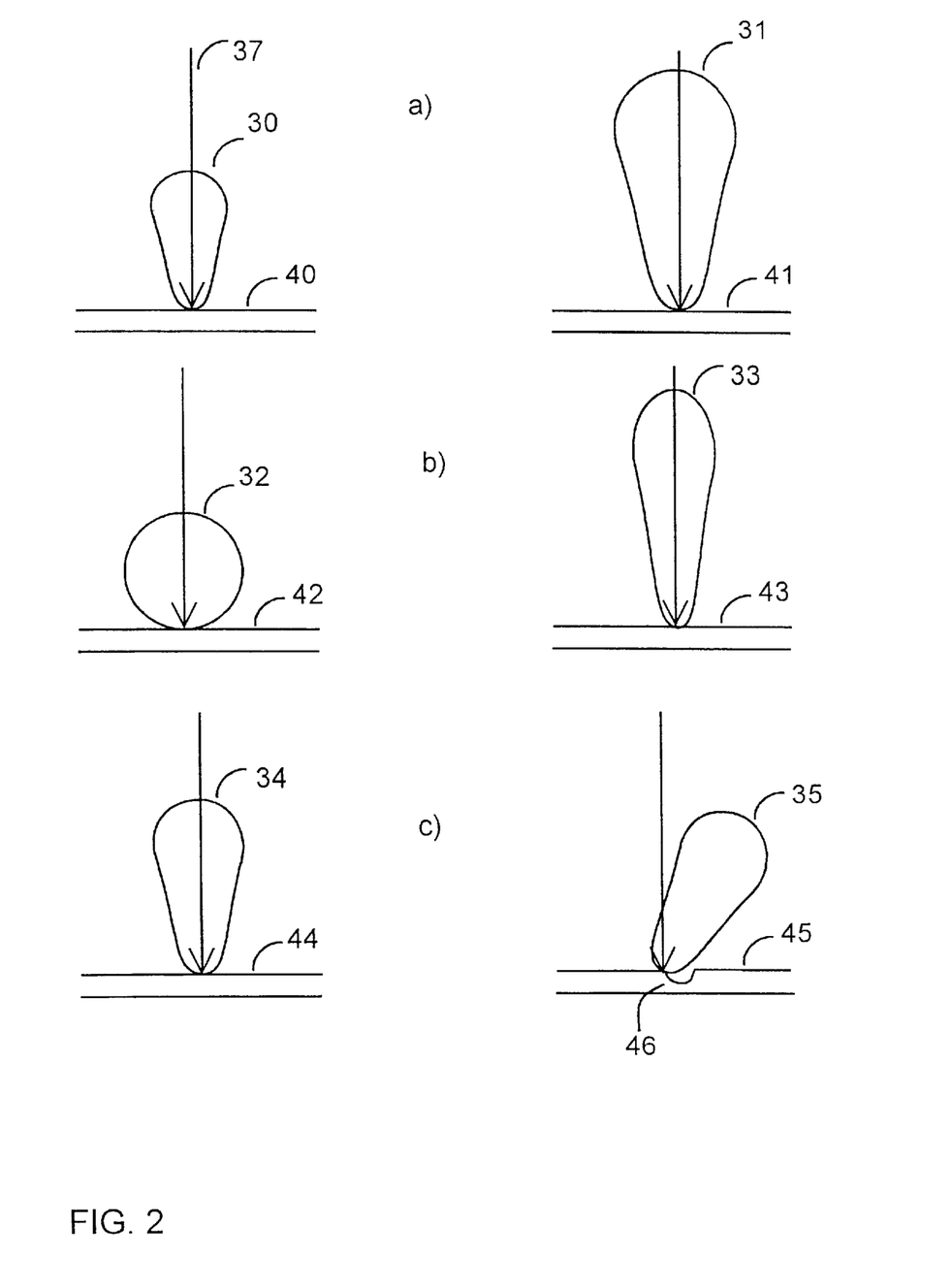
FIG. 2 illustrates how orthogonally incident light reemitted from the object's surface behaves on different surfaces.

FIG. 2 shows basic examples illustrating the physical behavior of light on a surface, which helps to understand the present invention. The different items of the figure show how orthogonally incident light 37 reemitted from the object's surface behaves on different surfaces. FIG. 2a shows the scattering of light reemitted from the objects' surfaces 40–41. The reflectivity of surface 40 is poorer than that of surface 41, wherefore the light reemitted 30 from surface 40 scatters more than the light reemitted 31 from surface 41. Another difference is that the amount of light 30 reemitted from surface 40 is smaller than the amount of light 31 remitted from surface 41.

FIG. 2b shows the configuration of light 32–33 reemitted from surfaces 42–43, which have different glossiness characteristics. The beam of light 32 reemitted from the surface 42 with poor glossiness is wider than the beam of light 33 reemitted from the surface 43 with better glossiness. The amounts of reemitted light 32–33 are here approximately equal.

FIG. 2c shows light 34–35 reemitted from surfaces 44–45, surface 44 being smooth and surface 45 being uneven 46. The uneven surface 45 makes the light 35 reemitted from the surface incline. The amounts of light 34–35 reemitted from the surfaces 44–45 are equal.

Figure 3:
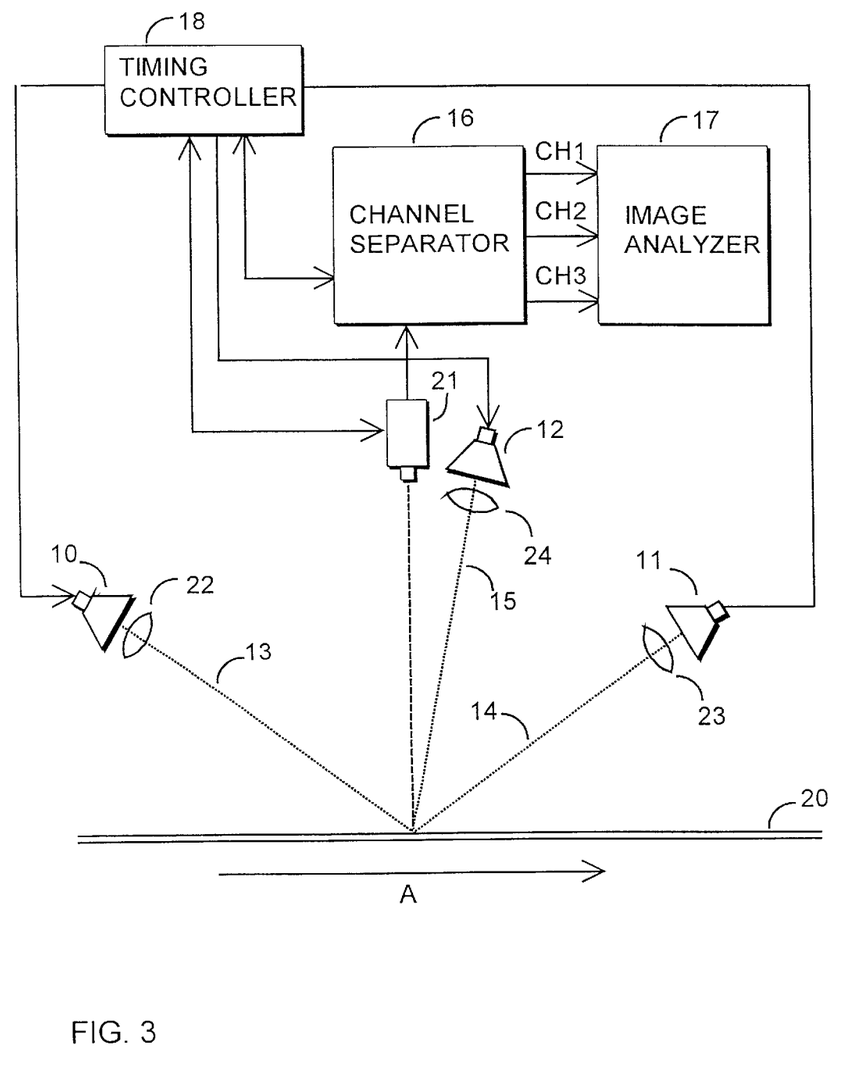
FIG. 3 shows an arrangement with one line scan camera and timing controller.

FIG. 3 shows an arrangement for inspecting the quality of the surface 20 of a moving object, the arrangement comprising light sources 10–12 of different illumination directions 13–15 for illuminating a region on the object's surface so that each illumination direction used has at least one light source; focusing means 22–24 for focusing the illumination; a line scan camera 21 for imaging the object's illuminated surface region; a channel separator 16; an image analyzer 17; and a timing controller 18 for synchronizing the operation of the above-mentioned components of the arrangement. The movement of the object is indicated by arrow A. If colors are irrelevant, the line scan camera 21 can be a monochrome camera. If colors are also to be measured, the line scan camera 21 used is a color camera.

In the method of FIG. 3, the operation of the light sources 10–12 illuminating at different times from different illumination directions 13–15 and that of the line scan camera 21 and of the channel separator 16 are synchronized by pulsing by the timing controller 18, the pulsing frequency of the light sources 10–12 illuminating at different times being >1 kHz. An imaging period is defined in the method by the timing controller 18; during each imaging period, the object's surface 20 is illuminated once from each illumination direction used. During each imaging period, a light beam from each illumination direction 13–15 is focused on the object's surface 20, at least partly on the same region, by the focusing means 22–24. In a preferred embodiment of the invention, the focusing means 22–24 are focusing and collimating lenses. When a monochrome camera is used as the line scan camera 21, and light sources 10–12 are pulsed from at least three illumination directions 13–15, the preferred embodiment of the invention can also be implemented such that the light beams from the different illumination directions 13–15 obtained during the imaging period are focused on different regions on the objects surface 20.

The pulsing frequency of the light sources 10–12 is determined on the basis of the speed of the moving object under inspection, so that the object's surface 20 can be inspected thoroughly. In other words, during a given imaging period, a region that is adjacent to the region that has been illuminated and imaged during the preceding imaging period is illuminated and imaged. The embodiment can also be implemented such that the surface region illuminated and imaged during the imaging period is not adjacent to the region illuminated and imaged during the preceding period but is spaced from it. The longer the distance, the larger the area on the object's surface 20 that will not be inspected at all, i.e. the quality of the whole surface will thus not be inspected.

The imaging frequency fk of the line scan camera 21 is defined by the formula $fk=n*fv$, where n is the number of illumination directions and fv is the pulsing frequency of the light sources of individual illumination directions. This is apparent from FIG. 3 which shows that when three illumination directions 13–15 are used to illuminate a region on the object's surface 20 at different times, the line scan camera 21 must be fast enough to image the object's surface region illuminated with at least one light source at a time from each illumination direction, i.e. the imaging frequency of the line scan camera 21 must be triple the pulsing frequency of the light sources of individual illumination directions 13–15 in a situation where three illumination directions 13–15 are used to illuminate a region on the surface 20 of the object to be imaged.

Figure 4:
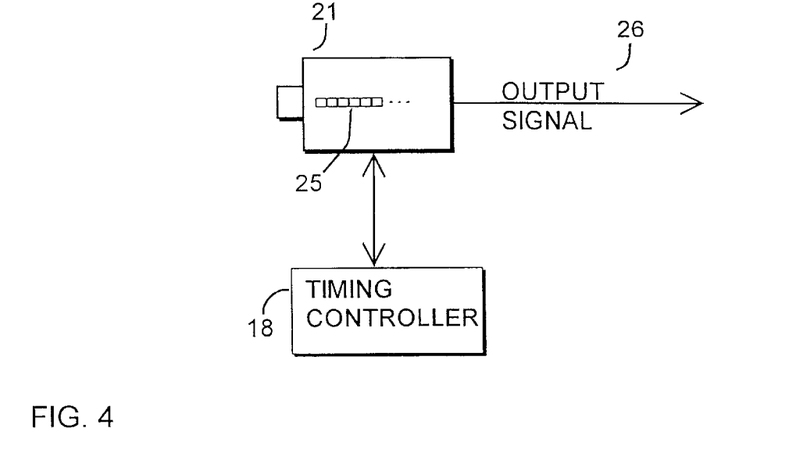
FIG. 4 is a schematic presentation of the operation of the line scan camera.

FIG. 4 is a schematic presentation of the operation of the line scan camera 21. The line scan camera 21 comprises sensors 25 for receiving beams of light emitted from the object's illuminated surface region. The arrangement comprises a timing controller 18 for imaging the object's surface region illuminated from each illumination direction with a line scan camera 21 as different successive lines, which form the output signal of the camera.

Figure 5:
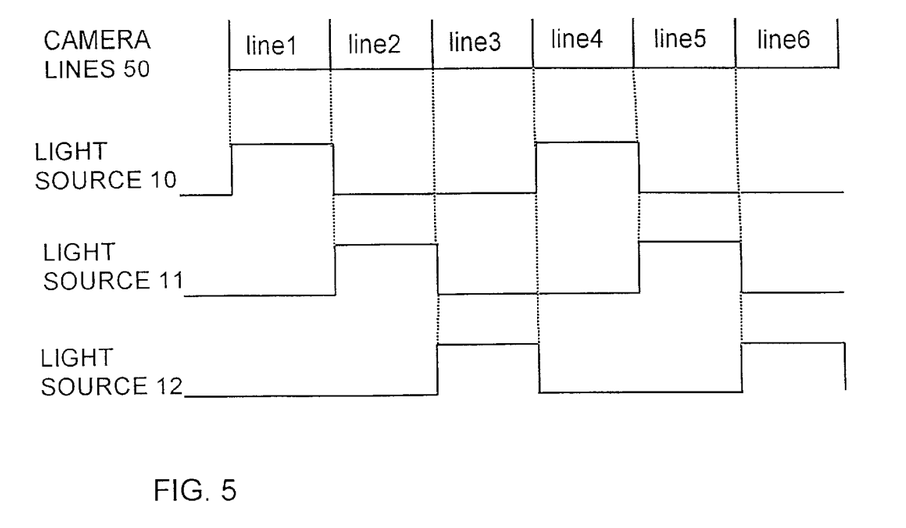
FIG. 5 is a pulsing scheme for the light sources of three illumination directions and an output signal of the line scan camera.

FIG. 5 shows a pulsing scheme for the light sources of different illumination directions 10–12, when the object's surface region is illuminated with light sources of three different illumination directions 13–15. The light sources of the different illumination directions 13–15 are pulsed so that the object's surface region is illuminated once from each illumination direction 13–15 during the imaging period. The beam of light from the illumination direction 13 from which the object's surface region is illuminated first is imaged with the line scan camera 21 as line1, the beam of light from the illumination direction 14 from which the object's surface is illuminated second is imaged as line2, and the beam of light from the illumination direction 15 from which the object's surface is illuminated third is imaged as line3. The line scan camera 21 thus images the object's surface region illuminated from each illumination direction 13–15 as different successive lines, which form camera lines 50 as the output signal of the line scan camera 21. Each line comprises image information on the object's illuminated surface region. In the example, when three different illumination directions 13–15 are used, the object's illuminated surface regions are imaged in the first imaging period as line1, line2 and line3, as mentioned above. In the imaging periods that follow, the object's illuminated surface regions are correspondingly imaged as fines in the same order of illumination directions 13–15: in the second imaging period, for example, as line4, line5 and line6. The lines are arranged as described above, imaging period by imaging period, until the last image has been taken. An example for this is a series of lines such as line1, line2, line3, line4, line5, line6, . . . , lineX, in which lineX stands for the image taken last. The series of lines is the output signal of the line scan camera 21 and can be, for example, a video signal.

Figure 6:
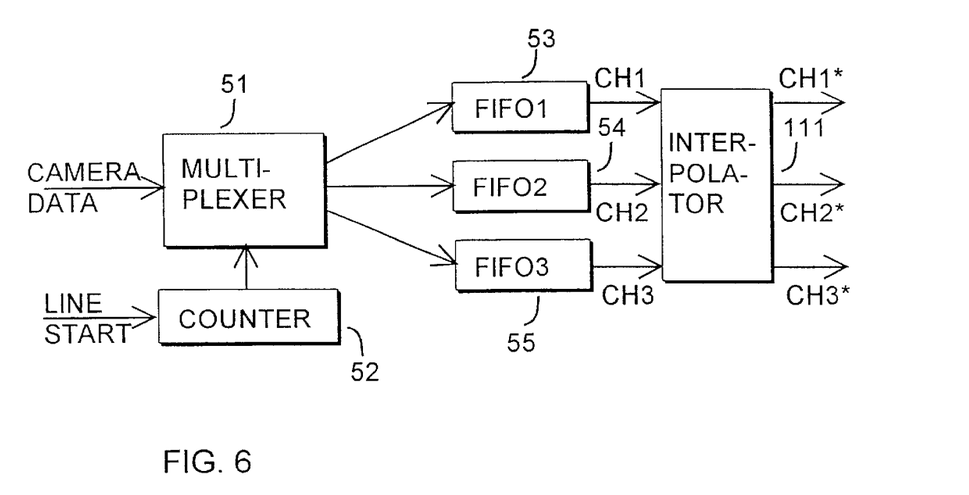
FIG. 6 shows the structure of a channel separator.

FIG. 6 shows a channel separator 16 for performing channel separation on the output signal of the line scan camera 21. The channel separator 16 comprises a multiplexer 51 for performing channel separation on the received output signal (camera data) of the line scan camera 21; a counter 52 for identifying the separated channels CH1, CH2, etc. correctly; and FIFO circuits 53–55 for satisfying the FIFO principle at the output of the channel separator 16. The channel separator further comprises an interpolator 111 for producing interpolated outputs CH1*, CH2*, etc. to the image analyzer 17. The interpolator 111 processes the images for each channel separately. The role of the interpolator 111 is to estimate the output signal for interlaced lines of a channel such that the (estimated) interlaced lines of the processed channel CH1 are perfectly registered with (measured) lines of another channel CH2 and therefore form the basis for pixelwise combinations of the images from CH1 and CH2. The simplest embodiments do not comprise the interpolator 111. The channel separator 16 can also comprise software run on a computer.

In FIG. 6 the multiplexer 51 performs channel separation on the output signal (camera data) of the line scan camera 21 to separate the lines of the series as so many channels as there are illumination directions that are used to illuminate the object's surface. Per each image period, the lines that contain image information on the object's surface regions illuminated from the same illumination direction are separated as the same channel. In other words, in the above example where the object's surface regions are illuminated from three different illumination directions 13–15 and the illuminated surface regions are imaged as line1, line2, line3, line4, line5, line6, . . . , lineX, the lines of the first imaging period are separated as follows: line1 is separated as channel CH1, line2 as CH2, and line3 as CH3. The counter 52 of the channel separator 16 receives a line start command from the timing controller 18, and on the basis of the command the counter 52 counts the lines to be separated as channels so that they are identified correctly. In other words, on the basis of the count conducted by the counter 52 the lines of the second imaging period separate in the example as the same channels in the corresponding order of illumination: line4 separates as CH1, line5 as CH2 and line6 as CH3. The channel separation continues in the same way until the end of the lines of the serie. The channels are supplied to image analysis from the FIFO circuits 53–55 on the FIFO principle (first in first out), i.e. from the series of lines line1, line2, line3, line4, line5, line6, . . . lineX, channel CH1 separated from the first line (line1) is outputted to the image analysis first, channel CH2 separated from the second line (line2) is outputted to the image analysis second, etc. Channels CH1, CH2, etc. separated from the lines of the next imaging periods are outputted to the image analysis or optionally to the interpolation carried out before the image analysis in the corresponding order according to the FIFO principle.

Figure 7:
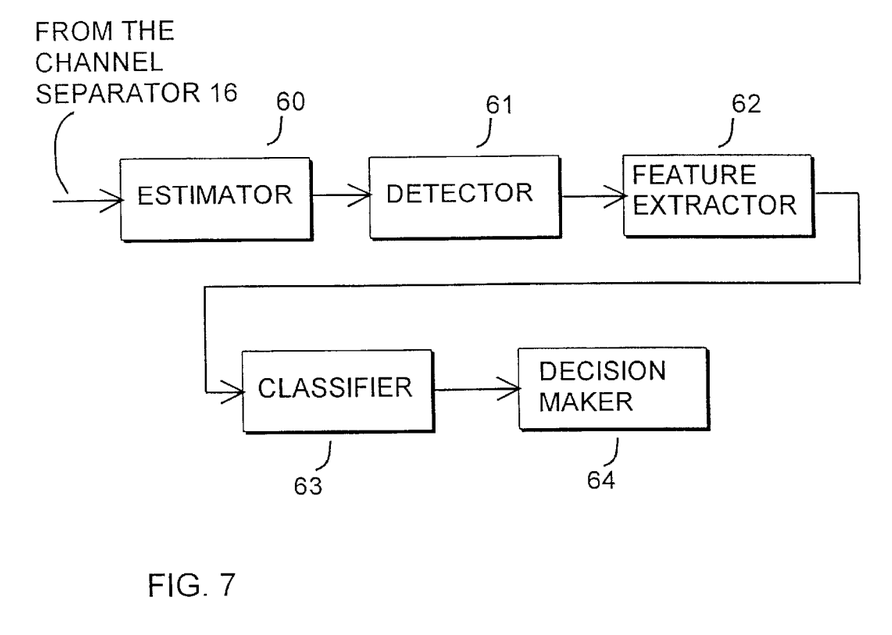
FIG. 7 shows the structure of an image analyzer.

The arrangement comprises an image analyzer 17 shown in FIG. 7 for performing image analysis on the basis of the channels obtained from the channel separator 16. The image analyzer 17 comprises an estimator 60 for estimating the image information of the channels on the physical properties of the object's surface region; a detector 61 for detecting physical flaws on the surface region; a feature extractor 62 for extracting the discriminating features of the physical flaws of the surface region; a classifier 63 for classifying the physical flaws (area, width, length, contrast of a defect) of the surface region; and a decision maker 64 for drawing the correct conclusions from the classified physical flaws of the surface.

The method of FIG. 7 comprises the step of performing an image analysis for inspecting the object's surface on the basis of the information contained in the channel-separated channels. The image analysis comprises analysis of image information on the object's illuminated surface region, contained in at least two channels. The image analysis comprises estimation of the image information of the channels on the physical properties of the object's surface region. On the basis of the estimation, the physical flaws of the surface are detected and classified, and the characteristics of the flaws are defined. On the basis of the characteristics defined, classification is performed, and on the basis of the classification, conclusions are drawn on the physical flaws of the surface.

Figure 8:
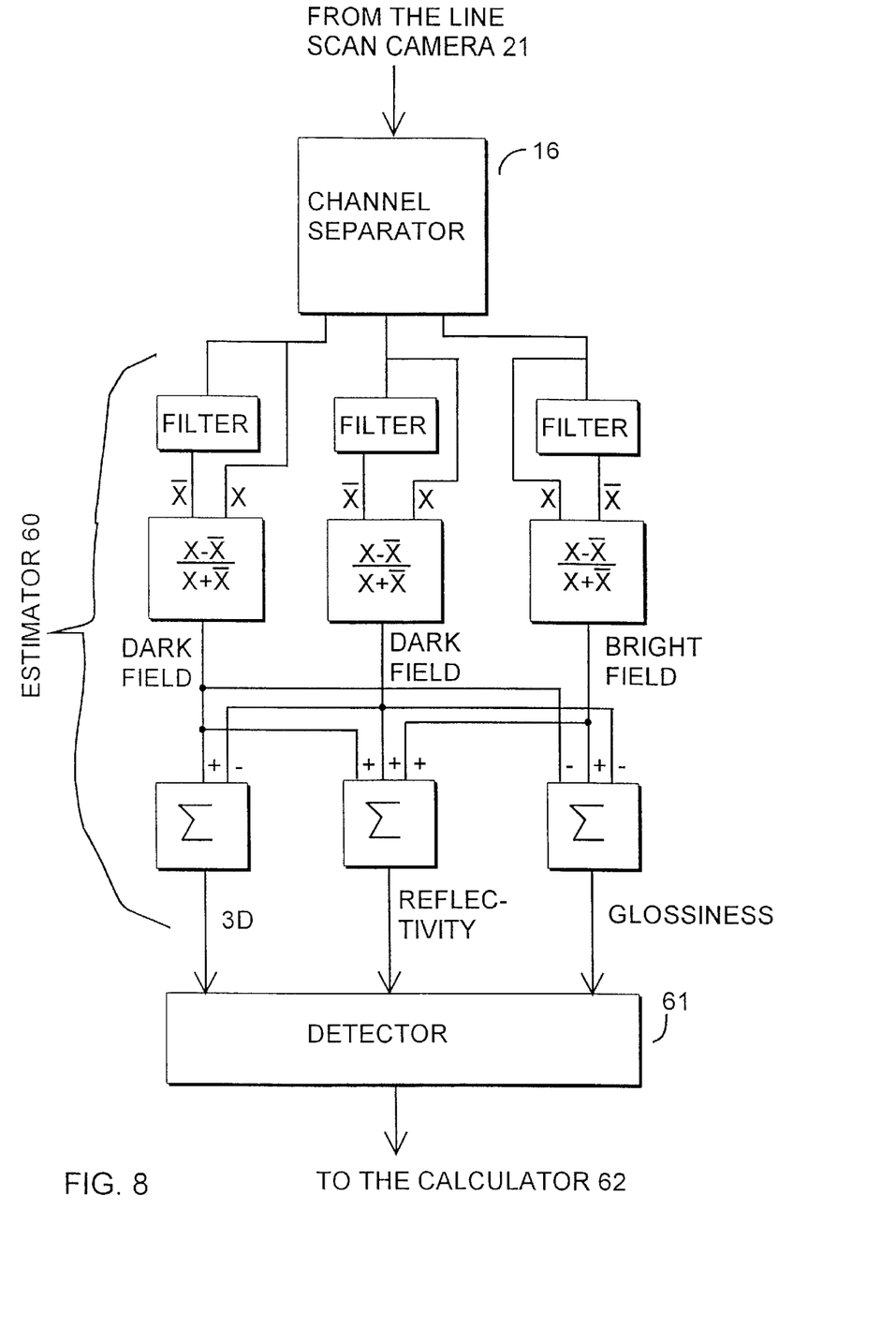
FIG. 8 illustrates channel comparison for the calculation of different characteristics of a surface region.

The image analysis is performed by comparing the image information of at least two channels with each other. To allow comparison, the channels of one and the same imaging period contain image information on at least partly the same surface region of the object. The channel comparison may reveal one of more of the following characteristics of the object's surface region: 3D profile (for example slopes), glossiness and reflectivity. In a preferred embodiment of the invention, the objects surface region can be dark-field-illuminated from at least two illumination directions, and optionally also bright-field-illuminated from at least one illumination direction. In FIG. 3, the surface of the moving object is illuminated from two dark field illumination directions 13–14 and one bright field illumination direction 15. The essential point in the preferred embodiment of the invention is that the light sources 10–12 of all the illumination directions 13–15 are as isochromatic as possible. The light sources are isochromatic if their wavelength range is essentially the same, i.e. when at least 50%, preferably more than 90%, of the illumination power of the light sources is within the same wavelength range. The changes in the color of the surface 20 do thus not distort the measurement of the characteristics of the surface region. FIG. 8 shows how the different characteristics of the surface region can be calculated accurately by channel comparison. Each illumination direction used is represented by a channel, which is first high-pass-filtered. The 3D profile of the object's surface region is calculated by comparing the image information of the channels of two dark field illumination directions 13–14 with each other so that one channel is subtracted from the other. The glossiness of the object's surface region is calculated by comparing the image information of the channels of all three different illumination directions 13–15 with each other so that the channels of the dark field illumination directions 13–14 are subtracted from the channel of the bright field illumination direction 15. The reflectivity of the object's surface region can be calculated by comparing the image information of the channels of all three illumination directions 13–15 so that all the three channels are added together.

In a preferred embodiment of the invention, the image information obtained from the same illumination direction for example in two successive imaging periods are separated as the same channel. The objects surface is checked by comparing the channels for example by comparing the image information obtained from illumination direction 14 with the image information obtained from illumination directions 13 and 15.

The arrangement comprises, for example, laser diodes and/or LEDs as the light sources 10–12 providing illumination at different times. In a preferred embodiment of the invention, the use of isochromatic pulsable light sources, such as laser diodes, and a monochromatic camera as the line scan camera 21 for inspecting the 3D characteristics of the surface 20 of a moving object eliminates the off-color problem, which renders the surface inspection considerably more reliable.

The use of laser diodes as light sources 10–12 allows better inspection of the surface 1 of a moving object, for example a hot moving surface, from a distance. The inspection from a distance here refers to inspection from a distance of at least one meter, but perhaps even of three meters. The object's movement is indicated by arrow A. The preferred embodiment of the invention is based on the idea that the beams of light emitted by the laser diodes are coherent, whereby the beams of light, i.e. the illumination, can be focused on a small area even from afar. In other respects, the arrangement and method comprise the same components and method steps as described above.

Figure 9:
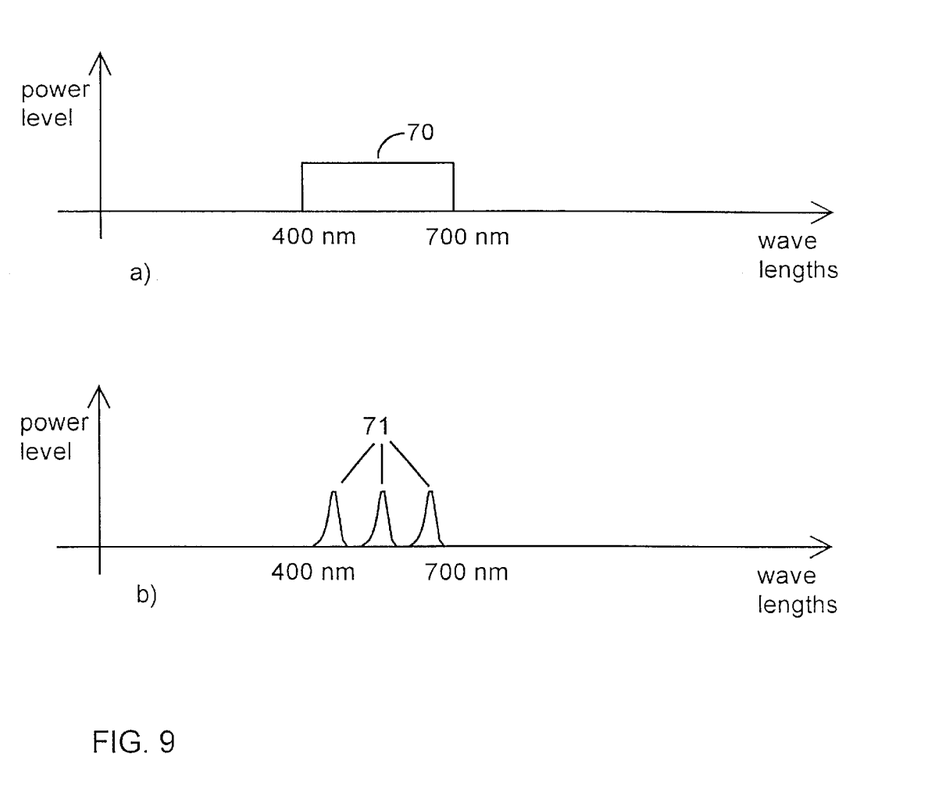
FIG. 9a shows the spectrum of the wavelength range of visible light.
FIG. 9b shows the spectra of the wavelength ranges of combined sources.

To determine the colors in a preferred embodiment of the invention, light sources 10–12 with a wide illumination spectrum, such as LEDs, or light sources with different illumination spectrums, i.e. of different colors, such as LEDs and/or laser diodes, are used in the illumination directions 13–15, and a color camera is used as the line scan camera 21. The most accurate color measurements are obtained with wide-spectrum light sources, which cover the whole wavelength range of visible light, 400 nm to 700 nm, as evenly as possible. This kind of spectrum 70 is shown in FIG. 9a. When less accuracy is considered sufficient, combined sources can be used in the color measurement, said sources being identical in each illumination direction used. The combined sources have different illumination spectra, i.e. they are light sources of different colors. FIG. 9b shows, by way of example, spectra of the combined sources 71 of one illumination direction. The spectra of the light sources in the other illumination directions used are identical, i.e. the light sources 10–12 are isochromatic. The light sources of different colors have essentially different wavelength ranges, whereby less than 50% of the illumination power of the light sources is within the same wavelength range. The wavelength range of the beam of light of a light source with a wide illumination spectrum is more than 50 nm wide. Another advantage brought about by the illumination of the surface regions from different illumination directions 13–15 at different times and the image analysis based on the image information obtained from the above illuminated surface regions by imaging in accordance with the invention is that no off-color problems occur, not even when combined sources are used in accordance with the above. Since the inspection of the surface allows the colors to be estimated correctly, the surface's 3D analysis, glossiness analysis and reflectivity analysis are rendered considerably more reliable. An indication of the improved reliability is, for example, that false alarms are avoided, which greatly speeds up the production process.

Plastic surfaces, for example, may differ slightly in color when they are inspected from different illumination directions. In a preferred embodiment of the invention, the use of pulsed light sources and a color camera as the line scan camera 21 enables a separate color measurement to be carried out in the object's each surface region illuminated from each dark field and/or bright field illumination direction 13–15. This is sometimes important in order to obtain sufficient information on the color characteristics of the surface under inspection.

The essential point in the preferred embodiments of the invention is how the object's surface is illuminated from different illumination directions 13–15. In the preferred embodiments of the invention, the illumination characteristics can also be brought about by operations and/or equipment that do not relate to light sources.

Figure 10:
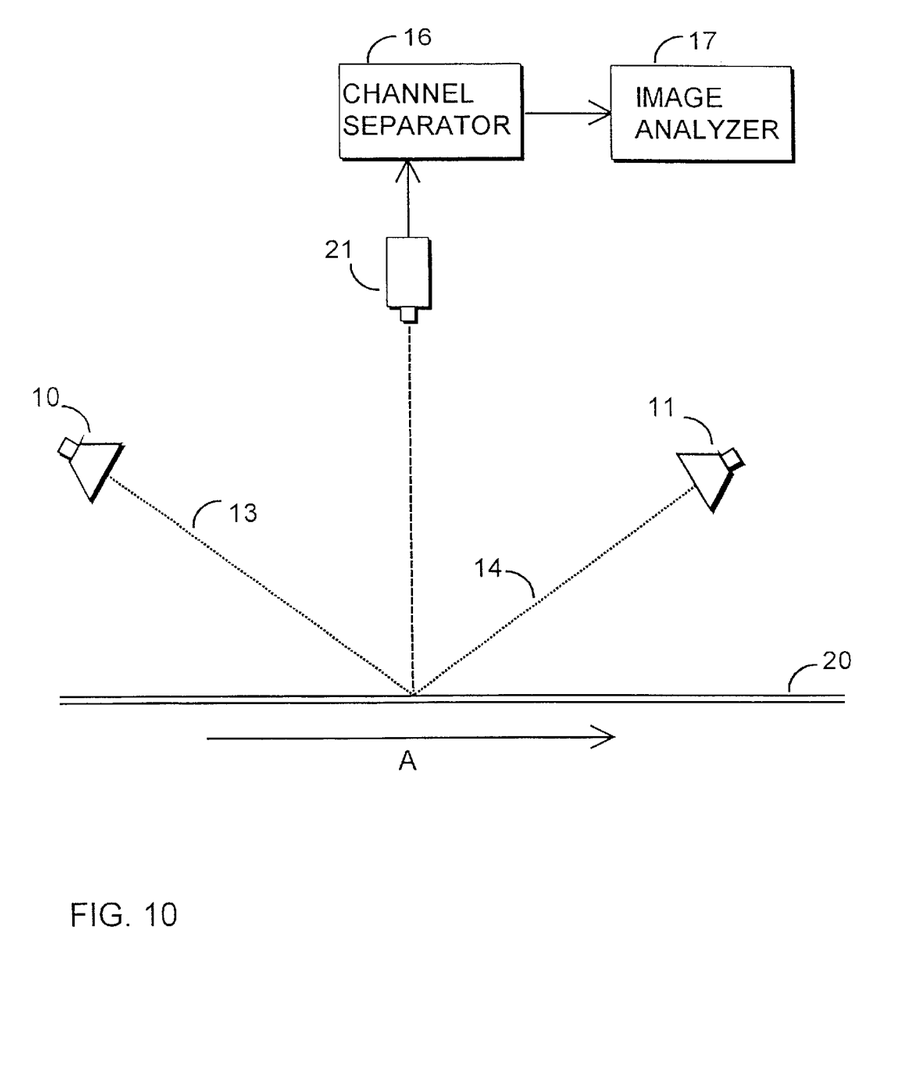
FIG. 10 shows an arrangement in which the surface under inspection is dark-field illuminated at different times from two different directions.

FIG. 10 shows a preferred embodiment of an arrangement and a method of the invention when the moving surface 20 under inspection is illuminated from two different illumination directions 13–14 at different times by dark field illumination. The object's movement is indicated by arrow A. When the object's surface regions are illuminated from two different illumination directions 13–14 at different times in accordance with the invention, the two images of dark-field-illuminated surface regions taken in the above situation during one imaging period contain a sufficient amount of imaging information for successful image analyses. In other respects the arrangement and method comprise the same components and method steps as described above.

Figure 11:
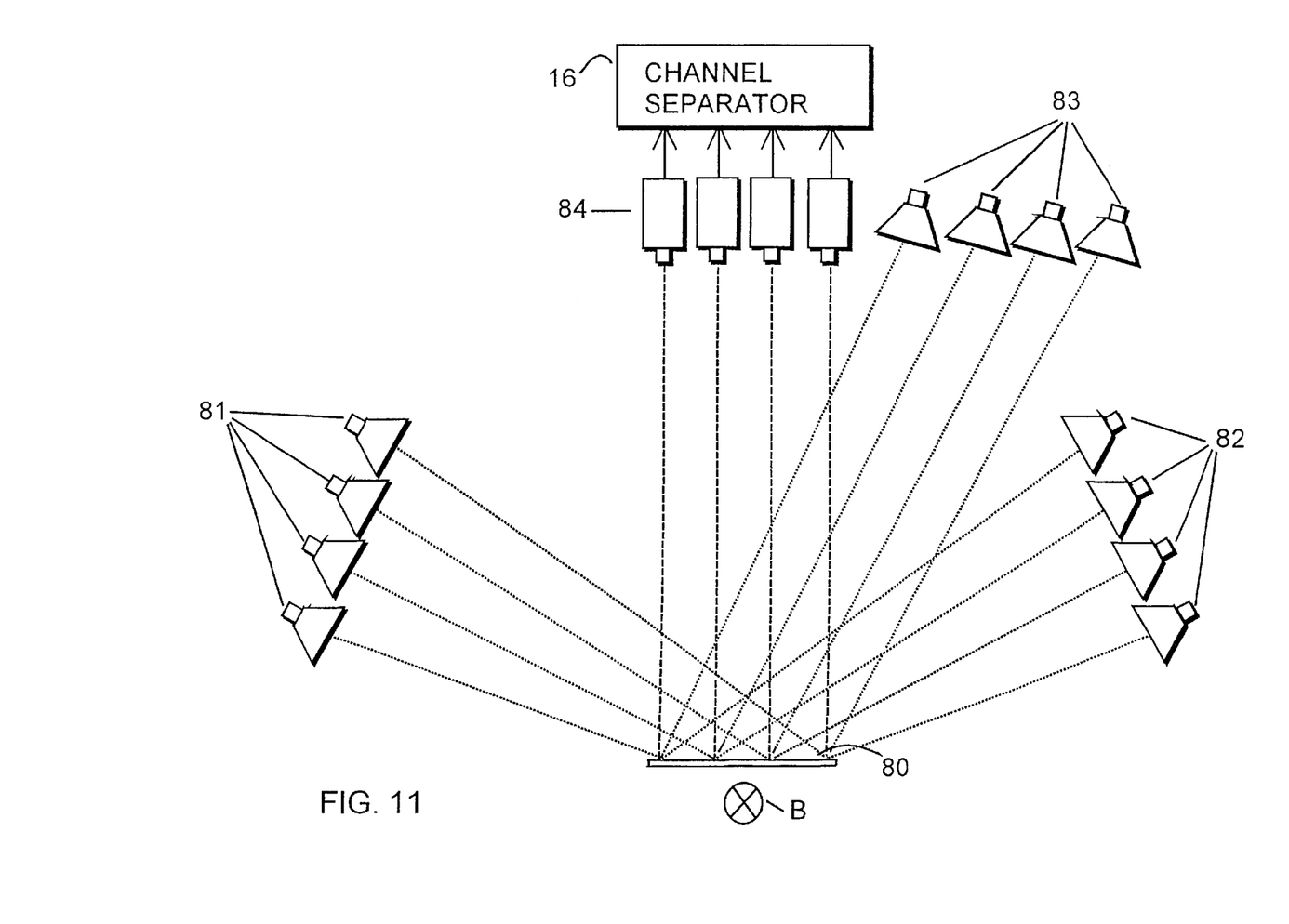
FIG. 11 shows an arrangement with four line scan cameras.

FIG. 11 shows a preferred embodiment of an arrangement for inspecting the surface 80 of a moving object, the arrangement comprising four line scan cameras 84 for imaging the surface regions of the moving object. The arrangement further comprises so many light sources 81–83 in the illumination directions that the whole width of a wide area 85 to be imaged by four line scan cameras 28–31 can be illuminated. The orthogonal movement of the object to be inspected is indicated by arrow B. In other respects the arrangement comprises the same components as described above.

In the preferred embodiment of the method illustrated in FIG. 11, adjacent surface regions of the moving object are imaged with four line scan cameras 84 arranged in spatially different places. The number of the light sources 81–83 in the illumination directions is designed to be so great that the entire width of the surface region of the moving object can be illuminated from each illumination direction in turn. In other respects the method comprises the same method steps as described above.

The preferred embodiment of FIG. 11 can be applied, for example, to inspection of a hot band. The object to be inspected is then a hot surface, which is illuminated with light sources 81–63 from the illumination directions and imaged with line scan cameras 84. The object's surface 80 is here inspected from a distance, and to guarantee sufficient illumination power, the light sources 81–83 must here be laser diodes.

When the 3D characteristics of the surface 80 are to be measured in a situation where the colors of the surface are not relevant, the preferred embodiment of the invention is implemented by color modulation and pulsing, combining the arrangements of FIGS. 10 and 11. In the embodiment, the objects surface is illuminated at different times from five different illumination directions 13, 14, 81, 82, 83, which provide two opposite pairs of dark field illumination directions 13, 14 and 81, 82, and a bright field illumination direction 83. Pulsed light sources of the same color, for example red, illuminate from illumination directions 13 and 14, and pulsed light sources that are mutually of the same color, for example green, illuminate from illumination directions 81 and 82. The bright field illumination direction 83 has at least one pulsed light source of a third color, for example blue. The comparison of the image information of the channels obtained from the above-mentioned illumination of the object's surface regions enables analysis of the surface's 3D characteristics and estimation of the surface's glossiness and color.

Figure 12:
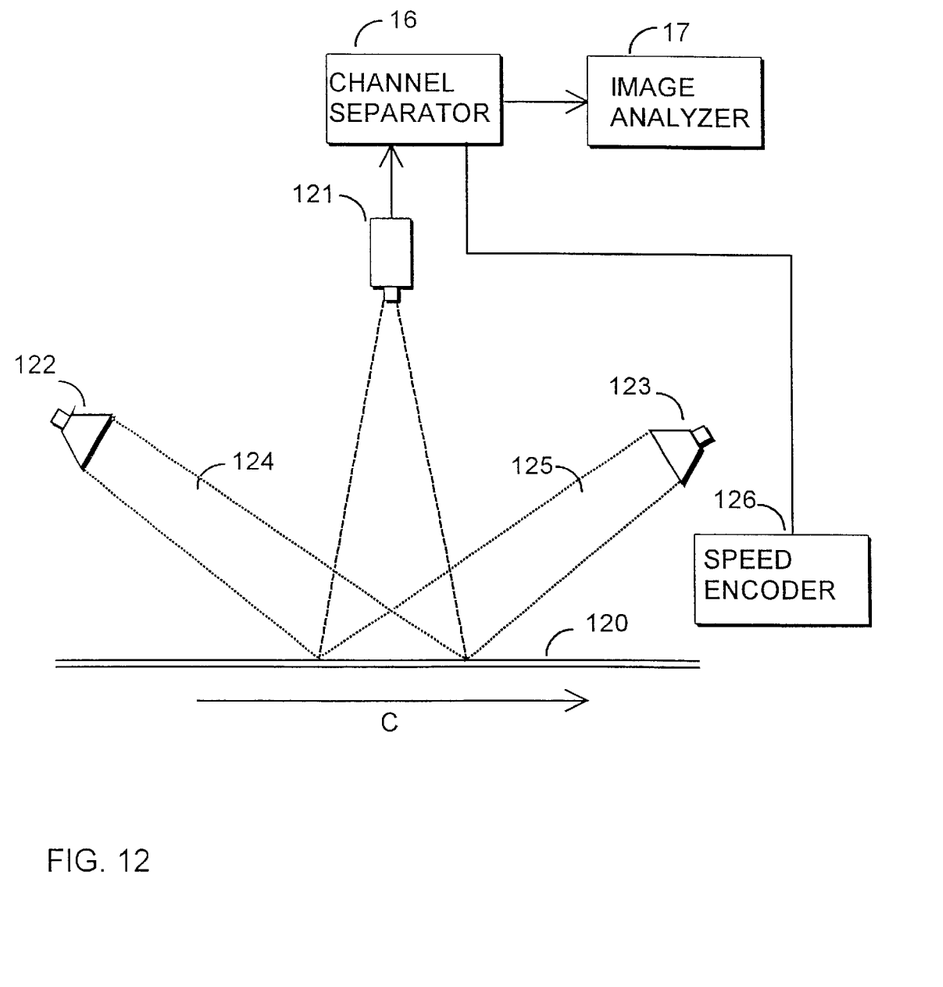
FIG. 12 shows an arrangement for inspecting the surface of a moving object using pulsed illumination and an area scan camera.

FIG. 12 illustrates inspection of a moving surface using pulsed illumination and an area scan camera 121. The object's movement is indicated by arrow C. The moving surface is imaged with an area scan camera 121 that produces one image area typically at a frequency of 50 or 60 Hz when cameras in accordance with the most general video standards are used; with special cameras the image frequencies can be faster or slower. The image area typically comprises hundreds of image lines (e.g. 250), which are illuminated simultaneously during the illumination period. Each image line comprises hundreds of pixels (e.g. 750). The surface 120 is illuminated evenly on the entire area to be imaged, i.e. the area seen by the camera 121, from at least two directions 124, 125 with light sources 122, 123 that can be pulsed, for example with a xenon strobe or LED light sources. The illumination pulse must be so short that the objects surface 120 does not have time to move, for example, more than by the breadth of one pixel. The light sources 122, 123 are pulsed so that light source 122 is pulsed once during the illumination period of the first image, and light source 123 is pulsed once during the illumination period of the second image, etc. in accordance with how many illumination directions are used. The images obtained from the camera are supplied to the channel separator 16, which forms continuous image line channels CH1, CH2, etc. from the images of each illumination direction. For further processing, the images of the different channels are interlaced to find out which image lines of each channel have been imaged at the same point of the surface 120. This is performed by measuring the speed of the surface 120 and by calculating how many image lines have transferred between the illumination pulses. The images can also be registered in the channel separator 16 by calculating the correlation between two images in the travel direction of the surface 120 on the basis of the image information. In order that the moving surface 120 could be inspected entirely with a single camera 121, the speed must not exceed the length of the region of the surface 120 seen by the camera 121 in the travel direction divided by the number of channels and the length of the ilumination period of one image. When the speed of the surface 120 is higher than this, more than one camera is used, the cameras imaging adjacent areas in the travel direction of the object. The channel separation can be implemented by software using a computer provided with an image capturing board, the measurement of the surface speed using a speed encoder 126 and the pulsing control of the light sources 122, 123 being also associated therewith. The position registered channels obtained in the above manner are processed further in a similar way as the channels produced in the line scan camera method.

The equipment needed for line scan camera 21 imaging comprises imaging optics, CCD line detectors as sensors, and signal processing electronics. The signal processing electronics comprises timing electronics, amplification electronics, AD conversion electronics and outlet connection electronics.

The timing controller 18 is implemented by electronics integrated into a camera interface board, and/or by discrete electronics.

The image analyzer 17 is implemented as computer software, and by a camera interface board and a preprocessing board. More specifically, the operating components of the analyzer are implemented as follows. The estimator 60 is implemented by a preprocessing board and/or by computer software. The detector 61 is implemented by a preprocessing board and/or by computer software. The feature extractor 62 is implemented by computer software, and so are the classifier 63 and the decision maker 64.

Although the invention is described above with reference to the example illustrated in the attached drawings, it is to be understood that the invention is not limited thereto but can be varied in many ways within the inventive idea disclosed in the attached claims.

What is claimed is:

1. A method for automatic inspection of the surface of a moving object, the method comprising the steps of illuminating a region on the object's surface from at least two different illumination directions, in each of which there is at least one light source, and imaging said object's illuminated surface region with a camera to provide image information for analysis, characterized in that the light sources in the different illumination directions are pulsed to illuminate the object's surface region at different times, the pulsing frequency being >1 kHz, the object's illuminated surface region is imaged as lines with a line scan camera in sync with the above pulsing; and wherein channel separation is performed on an output signal of the camera, and the channel separation is performed to provide so many channels as there are illumination directions in use.

2. A method as claimed in claim 1, characterized in that an imaging period is defined as a period during which the object's surface region is illuminated once from each illumination direction used.

3. A method as claimed in claim 2, characterized in that during each imaging period a beam of light is directed from each illumination direction on at least partly the same surface region of the object.

4. A method as claimed in claim 3, characterized in that the directing is performed using focusing and collimating lenses.

5. A method as claimed in claim 2, characterized in that during each imaging period a beam of light is directed from each illumination direction on a different surface region of the object.

6. A method as claimed in claim 1, characterized in that the imaging as lines is performed with at least one line scan camera.

7. A method as claimed in claim 6, characterized in that each line comprises image information on the object's illuminated surface region.

8. A method as claimed in claim 6, characterized in that the line scan camera images the object's surface region illuminated from each illumination direction as different successive lines, which form the output signal of the line scan camera.

9. A method as claimed in claim 1, characterized in that the line scan camera images the surface regions illuminated from each illumination direction as different lines.

10. A method as claimed in claim 1, characterized in that the output signal of the camera is a video signal.

11. A method as claimed in claim 1, characterized in that the channel separation is performed such that the lines that contain image information on the object's surface regions illuminated from the same illumination direction per imaging period are separated as the same channel.

12. A method as claimed in claim 11, characterized in that the object's surface is checked by comparing the channels using an interpolation method.

13. A method as claimed in claim 12, characterized in that the output signal of the line scan camera is estimated from the object's surface region from which the output signal of the line scan camera has not been measured.

14. A method as claimed in claim 1, characterized in that the object's surface region is dark-field-illuminated from at least two different illumination directions.

15. A method as claimed in claim 14, characterized in that the surface region is bright-field-illuminated from at least one illumination direction.

16. A method as claimed in claim 1, characterized in that light beams from the light sources in the different illumination directions have essentially similar wavelength ranges.

17. A method as claimed in claim 16, characterized in that when the wavelength ranges are essentially similar, more than 50% of each light beams' respective illumination power is within the same wavelength range.

18. A method as claimed in claim 17, characterized in that preferably more than 90% of each light beams' respective illumination power is within the same wavelength range.

19. A method as claimed in claim 1, characterized in that the channel separation is performed using a channel separator, and that the light sources of the different illumination directions, the camera and the channel separator are pulsed synchronously by means of a timing controller.

20. A method as claimed in claim 1, characterized in that an image frequency fk of the line scan camera is defined by a formula fk=n*fv, where n is the number of illumination directions and fv is the pulsing frequency of the light sources of individual illumination directions.

21. A method as claimed in claim 1, characterized in that the imaging is performed using at least one color camera.

22. A method as claimed in claim 1, characterized in that the imaging is performed using at least one monochromatic camera.

23. A method as claimed in claim 1, characterized in that the object's surface region is illuminated using at least one laser diode as the light source.

24. A method as claimed in claim 1, characterized in that the object's surface region is illuminated using at least one LED diode as the light source.

25. A method as claimed in claim 1, characterized in that the light beams from the light sources in different illumination directions have essentially different wavelength ranges.

26. A method as claimed in claim 25, characterized in that when the wavelength ranges are essentially different, more than 50% of each light beams' respective illumination power is within a different wavelength range.

27. A method as claimed in claim 1, characterized in that at least two cameras are arranged in spatially different places.

28. A method for automatic inspection of the surface of a moving object, the method comprising the steps of illuminating a region on the object's surface from at least two different illumination directions, in each of which there is at least one light source, and imaging said object's illuminated surface region with a camera to provide image information for analysis, characterized in that the light sources in the different illumination directions are pulsed to illuminate the object's surface region at different times and that the object's illuminated surface region is imaged with a camera in sync with the above pulsing; and wherein channel separation is performed on an output signal of the camera, and the channel separation is performed to provide so many channels as there are illumination directions in use.

29. A method as claimed in claim 28, characterized in that the imaging as images is performed with at least one camera.

30. A method as claimed in claim 29, characterized in that each image comprises image information on the object's illuminated surface region.

31. A method as claimed in claim 30, characterized in that the images form the output signal of the camera.

32. A method as claimed in claim 28, characterized in that the camera is an area scan camera.

33. A method as claimed in claim 28, characterized in that the channel separation is performed such that the images that contain image information on the object's surface regions illuminated from the same illumination direction per imaging period are separated as the same channel.

34. A method as claimed in claim 33, characterized in that the image analysis is performed on the basis of the image information contained in the channel-separated channels to inspect the object's surface.

35. A method as claimed in claim 34, characterized in that the image information of at least two channels on the object's illuminated surface region is analyzed in the image analysis.

36. A method as claimed in claim 35, characterized in that the analysis is performed by comparing the image information of at least two channels with each other.

37. A method as claimed in claim 36, characterized in that the channel comparison reveal one or more of the following characteristics of the object's surface region: 3D profile, glossiness and reflectivity.

38. A method as claimed in claim 36, characterized in that the channels are high-pass-filtered.

39. A method as claimed in claim 36, characterized in that a 3D profile of the object's surface region can be calculated by comparing the image information of the channels of two dark field illumination directions with each other so that one channel is subtracted from the other.

40. A method as claimed in claim 36, characterized in that a glossiness of the object's surface region can be calculated by comparing the image information of the channels of three different illumination directions with each other so that the channels of dark field illumination directions are subtracted from the channel of a bright field illumination direction.

41. A method as claimed in claim 36, characterized in that reflectivity of the object's surface region can be calculated by comparing the image information of the channels of all three illumination directions with each other so that all the three channels are added together.

42. A method as claimed in claim 28, characterized in that the object's surface region is illuminated using at least one gas discharge lamp as the light source.

43. An arrangement for inspecting the surface of a moving object, the arrangement comprising at least two light sources in at least two different illumination directions, i.e. at least one light source in each illumination direction used, for illuminating a surface region of the object under inspection; a camera for imaging the object's surface region; and an image analyzer for analyzing the image information acquired from the object's surface by imaging, characterized in that the light sources of the arrangement are light sources that illuminate the object's surface at different times from different illumination directions, and that the arrangement comprises at least one line scan camera for taking images of the surface region, and a timing controller for synchronous pulsing of the light sources and the at least one line scan camera, the pulsing frequency being >1 kHz; and wherein the line scan camera comprises the timing controller for imaging the object's surface region illuminated from each illumination direction as different successive lines, which form an output signal of the line scan camera; the arrangement comprises a channel separator for performing channel separation on the output signal of the line scan camera; the arrangement comprises the channel separator for performing channel separation such that each line is separated as a channel; and the arrangement comprises the channel separator for performing channel separation such that the lines that contain image information on the object's surface regions illuminated from the same illumination direction per imaging period are separated as the same channel.

44. An arrangement as claimed in claim 43, characterized in that the arrangement comprises the timing controller for defining an imaging period as a period in which the object's surface region is illuminated once from each illumination direction used.

45. An arrangement as claimed in claim 44, characterized in that the arrangement comprises directing means for focusing a light beam from each illumination direction used on at least partly the same region on the object's surface during the imaging period.

46. An arrangement as claimed in claim 45, characterized in that the directing means comprise focusing and collimating lenses.

47. An arrangement as claimed in claim 44, characterized in that the arrangement comprises directing means for focusing a light beam from each illumination direction used on a different region on the object's surface during the imaging period.

48. An arrangement as claimed in claim 43, characterized in that the arrangement comprises an interpolator for checking the object's surface by comparing the channels.

49. An arrangement as claimed in claim 48, characterized in that the system comprises an interpolator for estimating the output signal of the line scan camera from the object's surface region from which the output signal of the line scan camera has not been measured.

50. An arrangement as claimed in claim 43, characterized in that the channel separator comprises a multiplexer for channel separation, a counter for identifying the separated channels, and FIFO circuits for satisfying the FIFO principle at the output of the channel separator.

51. An arrangement as claimed in claim 43, characterized in that the arrangement comprises the timing controller for synchronizing the light sources of the different illumination directions, the at least one camera, and the channel separator.

52. An arrangement as claimed in claim 43, characterized in that the arrangement comprises the timing controller for defining an imaging frequency fk of the line scan camera by the formula fk=n*fv, where n is the number of illumination directions and fv is the pulsing frequency of the light sources of individual illumination directions.

53. An arrangement as claimed in claim 43, characterized in that the at least one line scan camera of the arrangement is a monochromatic camera.

54. An arrangement as claimed in claim 43, characterized in that the at least one line scan camera of the arrangement is a color camera.

55. An arrangement as claimed in claim 43, characterized in that the light source comprises at least one laser diode.

56. An arrangement as claimed in claim 43, characterized in that the light source comprises at least one LED.

57. An arrangement for inspecting the surface of a moving object, the arrangement comprising at least two light sources in at least two different illumination directions, i.e. at least one light source in each illumination direction used, for illuminating a surface region of the object under inspection; a camera for imaging the object's surface region; and an image analyzer for analyzing the image information acquired from the object's surface by imaging, characterized in that the light sources of the arrangement are light sources that illuminate the object's surface at different times from different illumination directions, and that the arrangement comprises at least one camera for taking images of the surface region, and a timing controller for synchronous pulsing of the light sources and the at least one camera; and wherein the arrangement comprises the timing controller for imaging the object's surface region illuminated from each illumination direction as different images with the camera, which form an output signal of the camera; the arrangement comprises a channel separator for performing channel separation on the output signal of the camera; the arrangement comprises the channel separator for performing channel separation such that each image is separated as a channel; and the arrangement comprises the channel separator for performing channel separation such that the images that contain image information on the object's surface regions illuminated from the same illumination direction per imaging period are separated as the same channel.

58. An arrangement as claimed in claim 57, characterized in that the channel separator comprises computer software.

59. An arrangement as claimed in claim 57, characterized in that the arrangement comprises an image analyzer for performing image analysis on the information of at least two channel-separated channels.

60. An arrangement as claimed in claim 57, characterized in that the light source comprises at least one gas discharge lamp.

61. An arrangement as claimed in claim 57, characterized in that the at least one camera is an area scan camera.

62. A method for automatic inspection of the surface of a moving object, the method comprising the steps of illuminating a region on the object's surface from at least two different illumination directions, in each of which there is at least one light source, and imaging said object's illuminated surface region with a camera to provide image information for analysis, characterized in that the light sources in the different illumination directions are pulsed to illuminate the object's surface region at different times, the pulsing frequency being >1 kHz, and that the object's illuminated surface region is imaged as lines with a line scan camera in sync with the above pulsing; and wherein channel separation is performed such that the lines that contain image information on the object's surface regions illuminated from the same illumination direction per imaging period are separated as the same channel; and wherein the object's surface is checked by comparing the channels using an interpolation method.

63. A method for automatic inspection of the surface of a moving object, the method comprising the steps of illuminating a region on the object's surface from at least two different illumination directions, in each of which there is at least one light source, and imaging said object's illuminated surface region with a camera to provide image information for analysis, characterized in that the light sources in the different illumination directions are pulsed to illuminate the object's surface region at different times, the pulsing frequency being >1 kHz, and that the object's illuminated surface region is imaged as lines with a line scan camera in sync with the above pulsing; and an image frequency fk of the line scan camera is defined by the formula fk=n*fv, where n is the number of illumination directions and fv is the pulsing frequency of the light sources of individual illumination directions.

64. A method for automatic inspection of the surface of a moving object, the method comprising the steps of illuminating a region on the object's surface from at least two different illumination directions, in each of which there is at least one light source, and imaging said object's illuminated surface region with a camera to provide image information for analysis, characterized in that the light sources in the different illumination directions are pulsed to illuminate the object's surface region at different times and that the object's illuminated surface region is imaged with a camera in sync with the above pulsing; and wherein channel separation is performed such that the images that contain image information on the object's surface regions illuminated from the same illumination direction per imaging period are separated as the same channel; and wherein the image analysis is performed on the basis of the image information contained in the channel-separated channels to inspect the object's surface; the image information of at least two channels on the object's illuminated surface region is analyzed in the image analysis; and the image analysis is performed by comparing the image information of at least two channels with each other.

65. An arrangement for inspecting the surface of a moving object, the arrangement comprising at least two light sources in at least two different illumination directions, i.e. at least one light source in each illumination direction used, for illuminating a surface region of the object under inspection; a camera for imaging the object's surface region; and an image analyzer for analyzing the image information acquired from the object's surface by imaging, characterized in that the light sources of the arrangement are light sources that illuminate the object's surface at different times from different illumination directions, and that the arrangement comprises at least one line scan camera for taking images of the surface region, and a timing controller for synchronous pulsing of the light sources and the at least one line scan camera, the pulsing frequency being >1 kHz; and wherein the arrangement comprises the timing controller for defining an imaging frequency fk of the line scan camera by the formula fk=n*fv, where n is the number of illumination directions and fv is the pulsing frequency of the light sources of individual illumination directions.

* * * * *